United States Patent [19]

McRae

[11] Patent Number: Plant 5,982

[45] Date of Patent: May 12, 1987

[54] ASIATIC LILY PLANT NAMED 'IMPALA'

[75] Inventor: Edward A. McRae, Boring, Oreg.

[73] Assignee: Melridge Inc., Gresham, Oreg.

[21] Appl. No.: 771,580

[22] Filed: Aug. 30, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler; John B. Lungmus

[57] ABSTRACT

A new Asiatic hybrid lily plant having large racemes of flowers of excellent form, large size, rich color and long persistence, both as cut flowers and on the plant. The flowers of this new plant are borne upright and are particularly characterized by their clear yellow color tone, as well as their size and substance, which are completely new in the Asiatic division of upright lilies suited to forcing. This new plant is highly resistant to disease and shows a high tolerance to virus. The bulbs of this plant may be precooled and forced for out-of-season cut flower production under glass; and the clone of this new variety is exceptionally vigorous, is a good grower and propagator, and is an excellent garden plant.

1 Drawing Figure

BACKGROUND OF THE INVENTION

This new variety of Asiatic lily originated as a seedling selected from a group of seedlings which resulted from my crossing of the cultivar "Sterling Star" with the cultivar "Connecticut Lemonglow" as the pollen parent in the course of breeding efforts carried on by me at Sandy, Oreg., since 1975 with the object of producing upright Asiatic lilies in the clear yellow color tone particularly suited to forcing for cut flower production, heretofore unknown in the lily breeding art.

The flowers of this new lily plant are particularly characterized by having a rich clear yellow color, unmarked by any orange tones, and are further distinguished for their unusually large size and excellent broad-tepalled form and substance. Additionally, this new Asiatic hybrid lily possesses a high degree of hybrid vigor, great hardiness, and disease resistance.

This new variety of Asiatic lily plant has been asexually reproduced by me and under my direction at Sandy, Oreg., and successive generations, produced by bulb scale propagation and natural propagation from bulblets, have demonstrated that the novel and distinctive characteristics of this new lily plant are fixed and hold true, under asexual propagation, from generation to generation.

DESCRIPTION OF THE DRAWING

This new variety of lily plant is illustrated by the accompanying photographic drawing which shows the open flower, together with some foliage and buds, to illustrate the flower form and tepal arrangement, and in particular the distinctive rich clear yellow tone which has been hand painted on the open flower to show the true flower color.

DESCRIPTION OF THE NEW VARIETY

The following is a detailed description of my new Asiatic hybrid lily plant with nomenclature according to The International Lily Register of The Royal Horticultural Society of London, England, and with color designations according to The R.H.S. Colour Chart published by The Royal Horticultural Society in 1966.

THE PLANT

Origin: Seedling.

Parentage:

*Seed parent.*—Lilium "Sterling Star".

*Pollen parent.*—Lilium "Connecticut Lemonglow" (unpatented).

Classification:

*Horticultural.*—Upright Asiatic hybrid lily, Division I-A of Horticultural Classification of Lilies by The Royal Horticultural Society of London, England.

*Commercial.*—Asiatic lily cultivar.

Form: Erect and stately single stem.

Height: About 90 to 110 cm. from bulbs about 15 to 18 cm. in circumference, under normal light conditions.

Growth: Vigorous and upright.

Foliage:

*Quantity.*—Abundant.

*Leaf size.*—About 7 to 10 cm. long and about 2 to 3 cm. wide.

*Leaf shape.*—Short, broad, and pointed (wide lanceolate).

*Texture.*—Leathery and glossy.

*Color.*—Medium green to dark green.

Bulbs:

*Size.*—Ranging up to 25 cm. in circumference, depending upon age.

*Color.*—White.

THE BUD

Form: Obtuse and oblong.

Size: About 8 to 8.5 cm. long and about 6 to 8 cm. in circumference immediately prior to opening.

Opening rate: The mature bud opens slowly, in response to light; generally this takes about one hour.

Color: Rich clear yellow when outer tepals first split open and also as they continue to unfurl.

Tepals:

*Color.*—Clear Yellow (R.H.S. 9-B/C to 8-B/C on inside and 9-C/D to 8-C/D on outside).

Peduncle: About 5 to 7 cm. long.

*Character.*—Erect

*Color.*—Dark green with light purple overlay.

THE FLOWER

Blooming habit: Annually, once and profusely in mid-season for Asiatic lilies.

Size: Large; about 16 to 17.5 cm. in diameter.

Borne: As a large raceme with 5 or 6 well spaced flowers when produced on stems from bulbs about 10 to 12 cm. in circumference; and with 7 to 11 flowers when produced on stems from bulbs from 12 to 15 cm. in circumference.

Shape: Shallow bowl shape with slightly recurved tepals.

Tepalage:

*Number.*—Six.

*Arrangement.*—Imbricated.

*Shape.*—Elliptic with acute tip and entire margins.

*Texture.*—Thick and leathery.

*Appearance.*—Shiny.

*Color.*—Clear Yellow, R.H.S. 9-B/C to 8-B/C, depending upon light conditions at the time of flowering with low light causing slightly lighter tones. Each of the tepals has a flush of deeper yellow, R.H.S. 12-A/B, covering an area of about 2 cm. wide and 2 cm. long immediately above the nectaries.

*Spotting.*—A band of small, deep magenta spots about 1 cm. wide immediately above the nectaries.

Color change: There is little color change as the flower ages, if the light levels are adequate for cut flower maintenance. The color may deepen slightly if the light levels weaken.

Pedicel:

*Length.*—About 7 to 10 cm. ascending at an angle of about 45°.

*Color.*—Medium to dark green with light purple overlay.

*Form.*—Sturdy and upright.

Persistence: The tepals stay on the stem for about three weeks.

Fragrance: None

Disease resistance: The flower and the plant are resistant to disease and, in particular, they are resistance to Fusarium bulb rot and to Botrytis blight, as observed in western Oregon.

Lasting quality: The flower is long lasting, both on the plant and as a cut flower.

REPRODUCTIVE ORGANS

Stamens:

*Number.*—Six.

*Arrangement.*—Typical of genus Lilium.

Anthers and pollen:

*Color.*—Bright Gold (R.H.S. 23-A).

Filaments:

*Length.*—About 5 cm.

*Color.*—Soft yellow.

Pistils:

*Number.*—One.

*Length.*—About 5 cm.

Stigma:

*Size.*—Medium.

*Color.*—Light yellow, occasionally lightly tinted in soft plum.

Character of ovary: Typical of genus Lilium.

THE FRUIT

Fertility: The fruit is fertile.

Shape: Ovoid.

Color at maturity: Soft brown, lightly overlaid with plum under cool conditions.

This new variety of Asiatic hybrid lily most nearly resembles the variety "Polyanna" but its flowers are a true rich yellow, lacking the gold flush of "Pollyanna". This new variety also has a superior inflorescence, forming a candelabrum of flowers on more evenly spaced, ascending pedicels.

I claim:

1. A new and distinct variety of hybrid Asiatic lily, substantially as herein shown and described, characterized in particular by its true rich yellow color tone and its relatively small amount of deep magenta maculation; its vigorous growth and propagation characteristics and the excellence of its flower form and tepal substance, its versatility both as a garden plant and as a plant produced from precooled bulbs and suited to forcing for cut flower production.

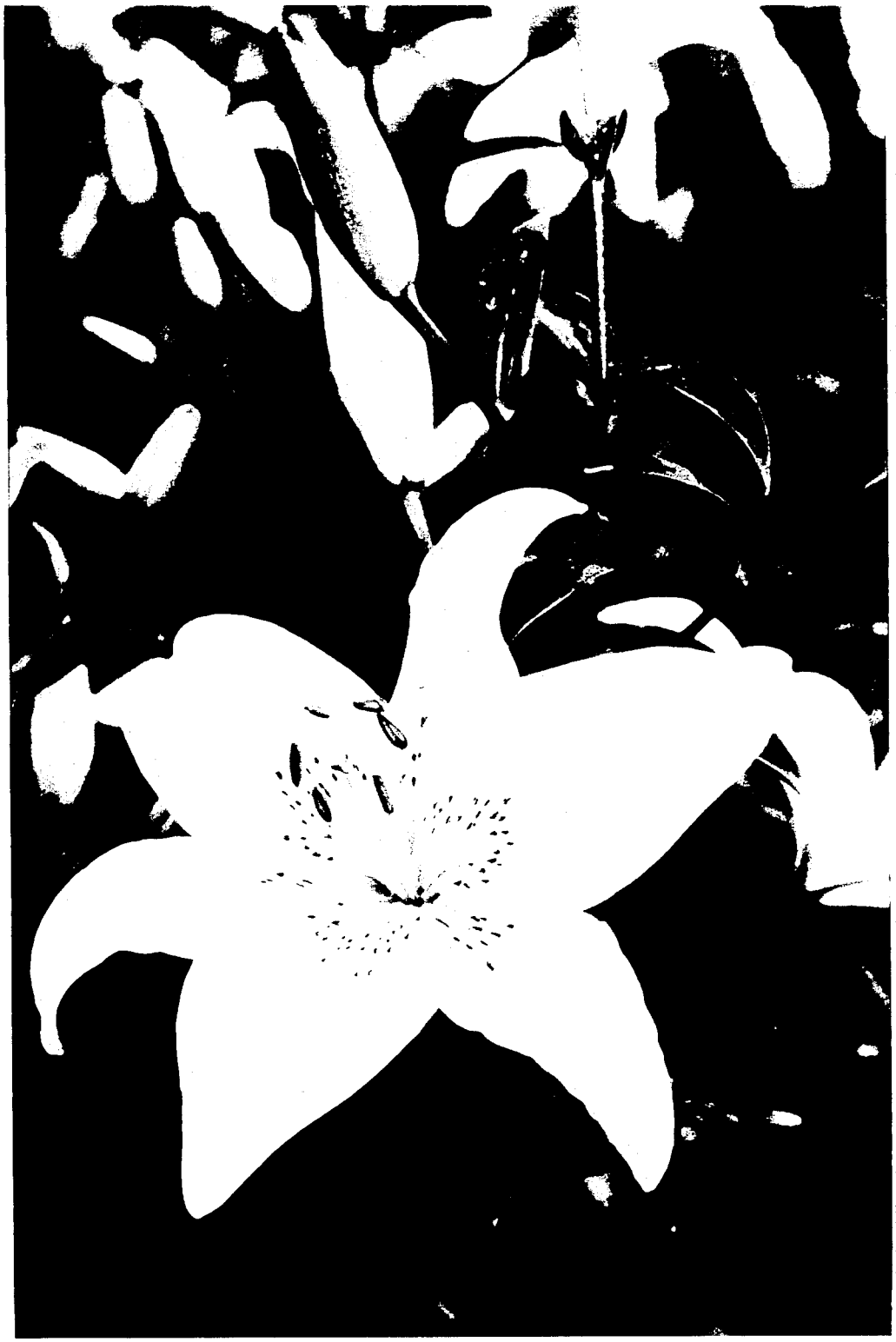

* * * * *